United States Patent [19]

Fiedler

[11] Patent Number: 4,605,984
[45] Date of Patent: Aug. 12, 1986

[54] STATIC CONTROL STRAP

[75] Inventor: Robert A. Fiedler, Santa Ana, Calif.

[73] Assignee: Beckman Industrial Corporation, Fulerton, Calif.

[21] Appl. No.: 762,249

[22] Filed: Aug. 5, 1985

[51] Int. Cl.$^4$ .............................................. H05F 3/02
[52] U.S. Cl. .................................................... 361/220
[58] Field of Search ............... 361/212, 220, 221, 223, 361/224; 174/5 R, 5 SB, 5 SG; 360/649, 658, 652, 568

[56] References Cited

U.S. PATENT DOCUMENTS

| 4,373,175 | 2/1983 | Mykkanen | 361/212 X |
| 4,459,633 | 7/1984 | Vandermark | 361/212 X |
| 4,475,141 | 10/1984 | Antonevich | 361/220 |
| 4,558,309 | 12/1985 | Antonevich | 340/658 X |

Primary Examiner—L. T. Hix
Assistant Examiner—Douglas S. Lee
Attorney, Agent, or Firm—A. A. Canzoneri; John E. Vanderburgh

[57] ABSTRACT

A grounding device for connecting the body of a person to a ground point to drain off electrostatic charge from the body of the person. The device includes a conductive band worn on the wrist of the user, a connecting cable and sensing and indicating circuitry for verifying the electrical continuity of the grounding device.

6 Claims, 6 Drawing Figures

STATIC CONTROL STRAP

BACKGROUND OF THE INVENTION

This invention relates to the field of electronic devices and more particularly to devices for dissipating electrostatic charge from the human body.

Many electronic components are susceptible to damage from electrostatic discharge. Damage generally occurs when sensitive components or the circuits in which they reside are handled by an electronics worker. Extremely high electrostatic potentials can build up in the human body and may be discharged through any electronic component or circuit that the worker touches. It is, therefore, a widely followed practice to provide electronics workers with means for dissipating electrostatic charge from the body. Typically, such means are in the form of a conductive strap which is worn about the wrist and capable of making electrical contact with the body. The wrist strap is connected to a suitable ground point (ideally, a dedicated earth ground) by means of a connecting cable. In this way, a path is provided by which any static charge in the body of the wearer is conveyed to ground and thereby harmlessly dissipated. It is only necessary for the worker to wear a grounding strap on one wrist to enable him to safely handle electronic devices with either hand, since the grounding device serves to dissipate the charge from the entire body.

A problem experienced by users of grounding wrist straps is that these devices are highly susceptible to failure through loss of electrical continuity between the wrist strap and the ground point. In such event, a user relying on a failed grounding device may unwittingly damage every charge sensitive device he handles. A widely observed solution to the problem is to test a grounding wrist strap before each wearing to verify its continuity. The observance of this practice will assure that a worker does not start work with a faulty strap. However, there is no assurance that an early failure will not occur and go undetected after the worker starts working.

Functional failure of grounding wrist straps occur with relatively high frequency because the connecting cable is subjected to constant flexure (occurring with each movement of the wearer's hand) and the device necessarily must employ very small wires or other conductors in order to be reasonably flexible and comfortable to the wearer. Furthermore, connecting cables are frequently subjected to forms of maltreatment that tend to hasten failure. Typical examples of maltreatment include subjecting the connecting cable to a strong pulling force when the wearer reaches for something beyond the reach of the cable; another form of maltreatment is to "run over" the connecting cable with the wheels of a rollered chair. These abuses are particularly destructive of cables employing carbon, carbonized fibers or other nonmetallic conductors.

A simple but obviously impractical solution to the above-described problem would be for manufacturers of grounding wrist straps to provide connecting cables of more robust proportions which could withstand all such likely forms of abuse. It will be readily seen that while heavier cable might assure greater functional reliability, it would also unduly restrict the movement of the wearer's hand and must, therefore, be considered impractical.

Another problem associated with the use of wrist grounding straps occurs when the user interrupts his activity and departs his work station. In such circumstance, the user would likely either remove the grounding strap from his wrist or detach the connecting cable therefrom. A problem arises when a worker returns to the work station to resume his activity but forgets to reconnect the grounding cable to the wrist strap. It is also possible that a worker might inadvertently connect the wrist strap to a source of electrical potential rather than a ground point, which could present a great hazard to the safety of the worker.

Accordingly, it will be seen that there is a need for improvements in the construction of grounding wrist straps to provide assurance of effectiveness in use and to protect the user against hazards associated with connecting wires to the human body. The present invention addresses the aforesaid needs and provides a static control wrist strap as described below and illustrated in the accompanying drawings.

SUMMARY OF THE INVENTION

The present invention is directed to grounding devices for connecting the body of a person to a ground point to drain off electrostatic charge from the body of the person. The disclosed grounding devices include means for monitoring electrical continuity between the using person and the ground point.

The grounding devices include a wrist band adapted to be worn on the using person's bare wrist. The wrist band is electrically conductive and adapted for making electrical contact with the body of the person. The wrist band further includes a connecting cable having first and second insulated wires, the first of which electrically connects the wrist band to a ground point. Signal generating means coupled with indicating means are electrically connected between the wrist band and the ground point through the second wire of the connecting cable. During operation of the grounding device, the first wire serves as a return path for signals from the signal generating means so that electrical continuity between the wrist band and the ground point is indicated by receipt of these signals by the indicating means.

BRIEF DESCRIPTION OF THE DRAWINGS

FIG. 5 is a schematic diagram illustrating the circuit of the grounding device of the present invention in yet another of its forms.

DESCRIPTION OF THE PREFERRED EMBODIMENTS

The present invention contemplates an improved grounding device for draining off electrostatic charge from the body of a person. An important aspect of the invention is the provision of a grounding device incorporating means by which the electrical integrity of the grounding device is continuously self-monitored and indicated to the user. Any open circuit fault in the circuit connecting the body of the wearer to a selected ground point is immediately detected and signalled to the user. Thus, a worker handling static sensitive devices may avoid commencing work with a defective body grounding device or may become aware when such a device fails in use.

Figure 1:
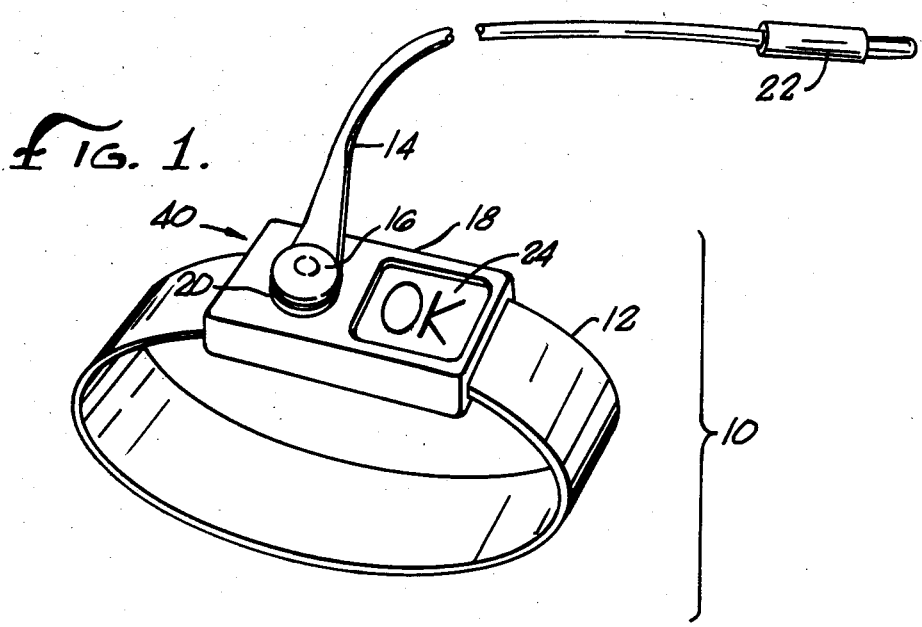
FIG. 1 is a perspective view of the grounding device of the invention in a first embodiment thereof.

Referring to FIG. 1, there is shown a perspective view of a grounding device constructed in accordance with one embodiment of the present invention and denoted in general by reference numeral 10. The grounding device includes a wrist band 12 which is adapted to be worn on the wrist, next to the skin of the using person. The wrist band 12 is electrically conductive and adapted for making electrical contact with the body of the user. A housing 18 is disposed on the wrist band 12 and contains electronic means for monitoring the electrical continuity between the wrist strap 12 and a ground point. One end of a connecting cable 14 is connected to the housing 18 through a suitable band connector means 16 and 20. The other end of the connecting cable 14 is connected to a selected ground point by ground connector means 22. The ground connector means 22 may be any suitable single circuit connector such as a banana plug, alligator clip, spade lug or the like. Similarly, the band connector means 16 and 20 may be any type of dual circuit connector such as a two-prong plug, phone plug or the like.

Figure 2:
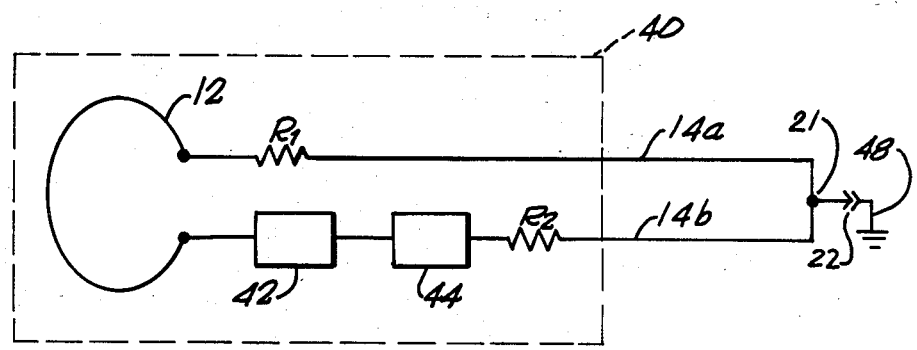
FIG. 2 is a schematic diagram illustrating the circuit of the grounding device of the present invention in one of its several forms.

Referring now also to FIG. 2, the grounding device of FIG. 1 is shown with greater detail in schematic form. In this schematic diagram and in subsequent diagrams, a portion of the circuit is enclosed within a dotted line rectangle 40 to denote the portion of the device which is situated at the wrist.

The connecting cable 14 includes first and second insulated wires 14a and 14b respectively. One end of wires 14a and 14b are both connected in common at point 21, which is in turn connected to ground point 48 through ground connector means 22. The other end of wire 14a is electrically connected to one end of the wrist band 12 through the band connector means 16 and 20. A current limiting resistor $R_1$ is interposed between the wrist band 12 and wire 14a. The resistor $R_1$ serves to protect the wearer of the grounding device against electric shock in the event the connecting cable 14 is inadvertently connected to a source of potential instead of a ground, or if the wearer contacts a source of potential while wearing the grounding device. A suitable resistance for resistor $R_1$ is 0.5 megohms.

It will be seen in FIG. 2 that the end of the wrist band opposite the end connected to $R_1$ is connected to one terminal of signal generating means 42. The other terminal of signal generating means 42 is connected to indicating means 44 which is in turn serially connected with a second current limiting resistor $R_2$ and insulated wire 14b. As will be apparent to those skilled in the art, the three elements 42, 44 and $R_2$ are in series with the wrist band 12 and wire 14b and, therefore, may be arranged in any order with the same result. A suitable resistance for resistor $R_2$ is 0.5 megohms.

Figure 3:
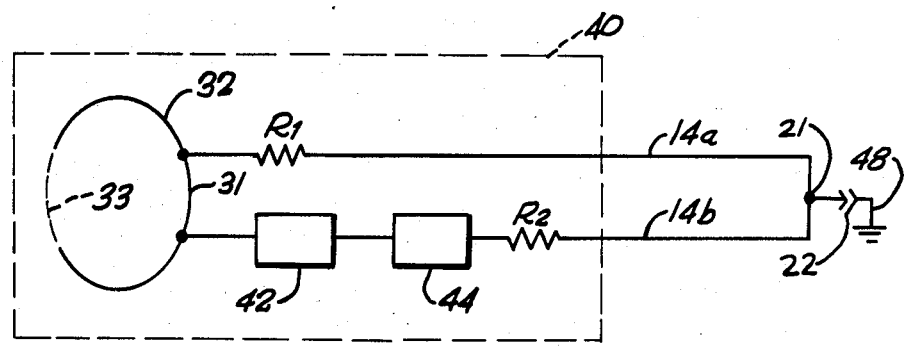
FIG. 3 is a schematic diagram illustrating one of the possible forms of the invention in greater detail.

Referring now to FIG. 3, the embodiment of FIG. 2 is shown in greater detail with respect to signal generating means 42 and indicating means 44 (the previously shown broken line rectangle 40 denoting the portion of the device situated at the wrist has been omitted). In this example, the signal generating means 42 comprises an astable multivibrator consisting of a battery B1, an integrated circuit 68 and timing elements consisting of capacitor $C_1$ and resistor $R_3$. In the instant example, the integrated circuit is designated as a type 4047A manufactured by RCA Corporation.

It should be understood that various modifications of the disclosed circuit are possible, as for example, various other integrated circuit devices or discrete components may be substituted. It is only required that the output be suited for driving the type of display employed—in the instant example, an alternating current for driving a liquid crystal display. Furthermore, battery $B_1$ may be replaced by a suitable photovoltaic device.

Indicating means 44 comprises a field-effect type liquid crystal display having front electrodes 72 and back plane electrode 74. In the example illustrated, the front electrodes 72 are formed to provide an indicia which signifies when there is electrical continuity in the grounding device circuit. The power requirements of the circuit are sufficiently low that the grounding device may be constructed, if desired, so as to be continually energized as in the manner of electronic wrist-watches. Although liquid crystal displays are well known, it is nevertheless pointed out for clarity that the back plane electrode 74 is depicted here schematically and that it actually comprises a planar layer spaced apart from and disposed in face-to-face relation to the front electrodes 72. It will be further apparent to those knowledgeable in the display art that polarizing and reflecting means may be required, to make the display visible under ambient lighting conditions depending upon the specific cell construction employed. Various modifications of the display may be employed such as making the back plane electrode reflective rather than transparent, thereby eliminating the necessity for placing a reflector behind the back plane. Another modification would be to construct a cell having a plain (unconfigured) front electrode and transparent back plane electrode with the desired indicia in the form of a label disposed on the exterior rear wall of the display cell. In operation, when the cell is energized, it functions as a simple light valve to expose the label indicia.

Figure 4:
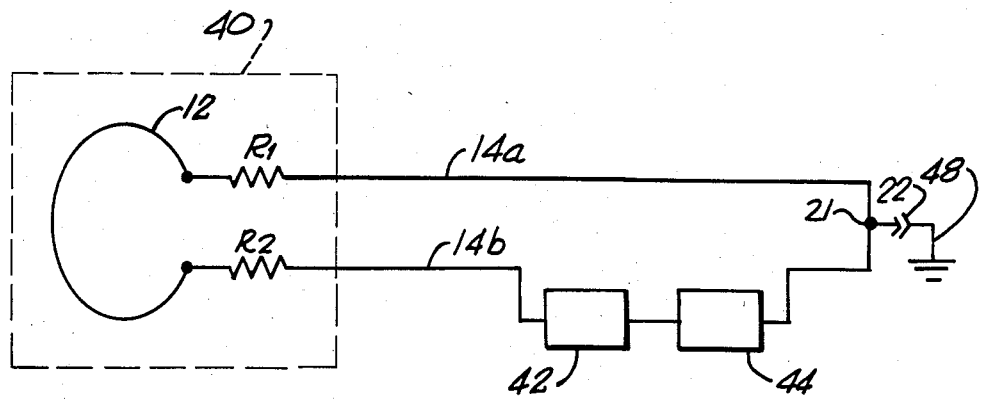
FIG. 4 is a schematic diagram illustrating the circuit of the grounding device of the present invention in yet another of its forms.
Figure 3:
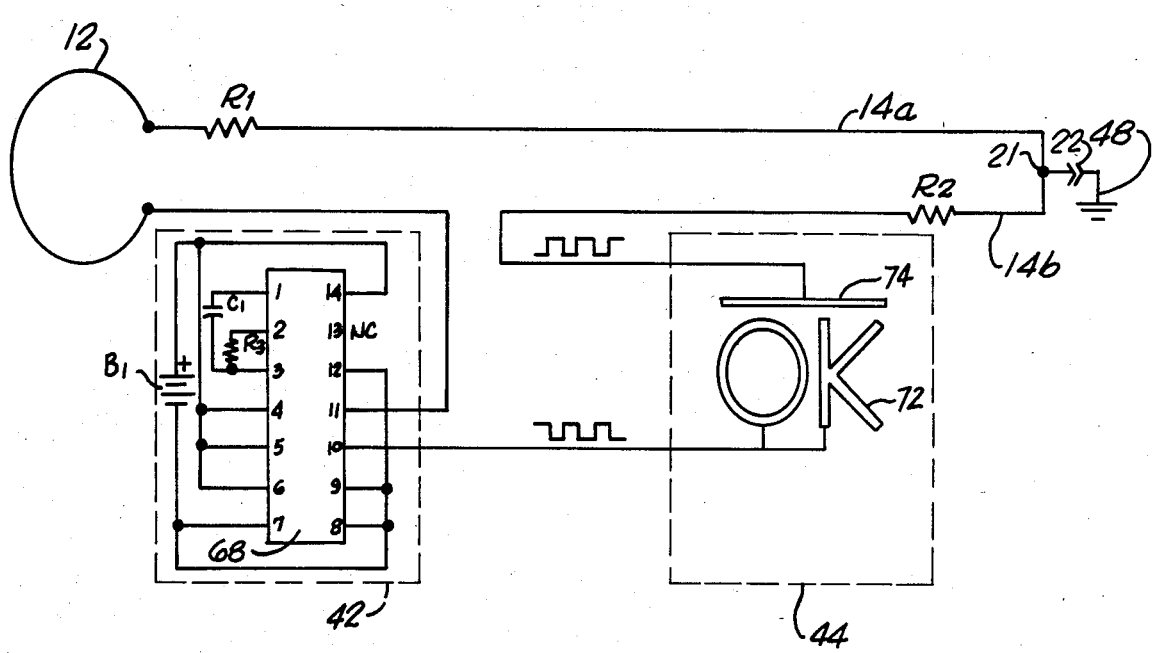

Referring now to FIG. 4, the invention is depicted in one of its modified forms. As shown by FIG. 4, the signal generating means 42 and indicating means 44 are not situated within the dotted line rectangle 40 which denotes the parts situated on the wrist band 12, but rather they are situated at a convenient remote location within the view of the wrist band wearer. Ideally, these monitoring elements could be housed in a suitable module at the user's work table and located along his line of vision. An advantage of this arrangement is that a visual indicator can be made larger and therefore more noticeable to the user. Additionally, the indicator means 44 may optionally include or be supplanted by an audible indicator, such as, for example, a piezo-electric sonic device.

Referring now to FIG. 5, the invention is depicted in yet another form. Unlike the previously disclosed embodiments of the present invention, in the embodiment of FIG. 5 the wrist band 32 is not connected at its end points to the insulated wires 14a and 14b of the connecting cable. Instead, a portion of the wrist band 32 which is denoted by reference numeral 31 is connected in the circuit loop defined by wires 14a, 14b, resistors $R_1$, $R_2$ and signal generating means 42 and indicating means 44.

In certain of the alternate forms in which the invention may be practiced, the arrangement of FIG. 5 will have best application. One such form is where the wrist band 32 is constructed in the form of a spring-type metal clasp, open (rather than continuous) in the region depicted by dotted lines 33. In this form, sometimes referred to as a "spring bracelet," the user is assured that the one-piece metal wrist band has extremely low resistance and is electrically continuous throughout its length. Therefore, unlike a wrist band made of a nonmetallic fiber or fabric, there is no necessity for monitoring electrical conduction throughout the entire length of the solid metal band. Other wrist band configurations which are suited to the circuit arrangement of FIG. 5 include wrist bands formed as an expandable wire coil and those formed as an expandable link bracelet such as commonly employed for wristwatches.

Figure 6:
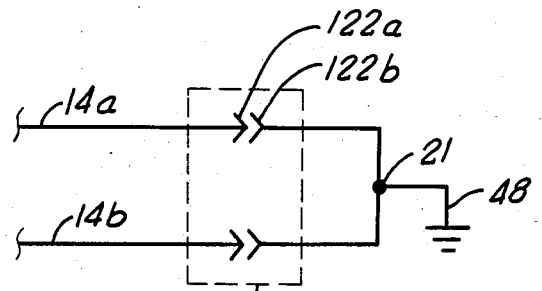
FIG. 6 is a schematic diagram of a portion of the circuit illustrated in FIGS. 1-5 showing means for detachably joining the circuit between ground point and wrist band.

FIG. 6 depicts a modification which is applicable to the circuits of FIGS. 1-5. FIG. 6 is a partial schematic diagram of only the right hand side of these circuits. In FIG. 6, a dotted line rectangle encloses a two-circuit connector 122. The connector 122 includes mating halves designated 122a and 122b. The two 122a halves are connected to respective wires 14a and 14b of the connecting cable 14 and the two 122b halves of connector 122 are connected in common at point 21 and from thence to the ground point 48.

An advantage residing in the use of the two-circuit connector 122 is that it prevents the indicating means 44 from signaling a condition of servicability unless the connecting cable 14 is connected to ground point 48. It will be readily seen that the current return path to the indicating means 44 is completed only when the "a" and "b" halves of connector 122 are joined. Thus, in cases where it is desired to have a detachable connection at the ground point, the user may employ the arrangement of FIG. 6. By so doing, the user safeguards himself against any inadvertent failure to connect the connecting cable to the ground point. Similarly, the indicating means 44 will signal the user of any subsequent interruption occuring in the connection to the ground point.

While in accordance with the patent statutes there has been described what is at present considered to be the preferred embodiments of the invention, it will be understood by those skilled in the art that various changes and modifications may be made therein without departing from the invention and is, therefore, the aim of the appended claims to cover all such changes and modifications as fall within the true spirit and scope of the invention.

I claim:

1. A grounding device for connecting the body of a person to a ground point to drain off electrostatic charge from the body of said person comprising:
    a wrist band adapted to be worn on a bare wrist of a person using said grounding device, said wrist band being electrically conductive and adapted for making electrical contact with the body of said person;
    a connecting cable having first and second insulated wires;
    one end of said first and second wires being electrically connected at a common ground point;
    an end of said first wire opposite said one end being electrically connected to said wrist band;
    signal generating means coupled with indicating means electrically connecting said wrist band to said ground point through said second wire, said first wire serving as a return path for signals from said generating means so that electrical continuity between said wrist band and said ground point is indicated by receipt of said signals by said indicating means.

2. The grounding device defined by claim 1, wherein said signal generating means comprises an astable multivibrator including a voltage source.

3. The grounding device defined by claim 2, wherein said indicating means comprise a liquid crystal display.

4. The grounding device defined by claim 1, further including first and second current-limiting resistors, said first resistor connected intermediate said wrist band and said first wire; said second resistor connected intermediate said wrist band and said second wire.

5. The grounding device defined by claim 1 further including a housing disposed on said wrist band and wherein said signal generating means and indicating means are contained by said housing.

6. The grounding device defined by claim 1 further including a two-circuit connector disposed in said connecting cable between said common ground point and said wrist band for detachably connecting said connecting cable and said ground point.

* * * * *